United States Patent [19]

Davenport et al.

[11] Patent Number: 5,466,869
[45] Date of Patent: Nov. 14, 1995

[54] PROCESS FOR PERPARING 4-HYDROXYACETOPHENONE OXIME

[75] Inventors: Kenneth G. Davenport, Corpus Christi, Tex.; Roger A. Sheldon, Rijswijk; Joel Le Bars, Den Haag, both of Netherlands; Werner H. Mueller, Charlotte, N.C.

[73] Assignee: Hoechst Celanese Corporation, Somerville, N.J.

[21] Appl. No.: 332,240

[22] Filed: Oct. 31, 1994

[51] Int. Cl.⁶ .................................................. C07C 249/04
[52] U.S. Cl. .................................................. 564/265
[58] Field of Search .................................................. 564/265

[56] References Cited

U.S. PATENT DOCUMENTS

| | | | |
|---|---|---|---|
| 4,410,501 | 10/1983 | Taramasso et al. | 423/326 |
| 4,745,221 | 5/1988 | Roffia et al. | 564/267 |
| 4,794,198 | 12/1988 | Roffia et al. | 564/267 |
| 4,968,842 | 11/1990 | Padovan et al. | 564/253 |
| 5,041,652 | 8/1991 | Padovan et al. | 564/267 |
| 5,227,525 | 7/1993 | Tonti et al. | 564/267 |

*Primary Examiner*—Peter O'Sullivan
*Attorney, Agent, or Firm*—James J. Mullen; Donald R. Cassady

[57] ABSTRACT

A catalytic process for preparing 4-hydroxyacetophenone oxime by reacting 4-hydroxyacetophenone with $NH_3$ and $H_2O_2$ in the liquid phase, in the presence of a catalyst substantially consisting of a titanium-containing molecular sieve such as a highly crystalline substance, containing $SiO_2$ and having a zeolitic structure.

10 Claims, No Drawings

PROCESS FOR PERPARING 4-HYDROXYACETOPHENONE OXIME

BACKGROUND OF THE INVENTION

1. Field of the Invention

The present invention relates to the production of 4-hydroxyacetophenone (4-HAP) oxime by the conversion of 4-HAP under ammoximation conditions.

2. Description of Related Art

The following prior art references are disclosed in accordance with the terms of 37 CFR 1.56, 1.97, and 1.98.

U.S. Pat. No. 4,524,217 (issued Jun. 18, 1985) discloses a process for producing N-acyl-hydroxy aromatic amines wherein the intermediate product is a ketoxime derived from a hydroxy aromatic ketone such as 4-HAP.

U.S. Pat. No. 4,560,789 (issued Dec. 24, 1985) discloses a process for producing 4-acetoxyacetanilide wherein the intermediate is hydroxyacetophenone oxime which is derived from 4-HAP.

U.S. Pat. No. 4,994,613 discloses a process for preparing 4-HAP oxime by the conversion of 4-HAP utilizing hydroxylamine.

U.S. Pat. No. 4,410,501 discloses a method for preparing a porous crystalline synthetic material comprised of silicon and titanium oxides.

U.S. Pat. Nos. 4,745,221, 4,794,198, and 4,968,842 all disclose a method for preparing cyclohexanone oxime by reacting cyclohexanone with $NH_3$ and $H_2O_2$ in the presence of a catalyst.

All of the above-cited prior art (and any other references/ patents disclosed hereinafter) are incorporated herein by reference in their entirety.

SUMMARY OF THE INVENTION

The present invention provides a novel catalytic process for preparing 4-HAP oxime by subjecting 4-HAP to suitable ammoximation conditions (such as with $NH_3$ and $H_2O_2$ in the liquid phase), characterized in that the catalyst substantially consists of a molecular sieve, preferably a titanium-containing molecular sieve such as a highly crystalline substance containing $SiO_2$ and having a zeolite structure.

DETAILED DESCRIPTION OF THE INVENTION

4-Hydroxyacetophenone (4-HAP) oxime is used to prepare N-acetyl-paraaminophenol (APAP) which is a commercially significant and important analgesic.

A process for the preparation of APAP utilizing the Beckmann rearrangement of the 4-HAP oxime is disclosed and claimed in U.S. Pat. No. 4,524,217.

One key step in the production of APAP, as set forth in U.S. Pat. No. 4,524,217 involves the preparation of 4-HAP oxime by reacting 4-HAP with hydroxylamine salt, e.g. hydroxylamine sulfate, and caustic to form the ketoxime of the ketone and then subjecting said 4-HAP ketoxime to a Beckmann rearrangement in the presence of a catalyst to form APAP.

As pointed out at column four of U.S. Pat. No. 4,524,217, the conversion of 4-HAP oxime is accomplished by contacting 4-HAP with a hydroxylamine salt such as hydroxylamine hydrochloride, hydroxylamine sulfate (HAS), hydroxylamine bisulfate, or hydroxylamine phosphate in a base such as ammonium hydroxide, potassium hydroxide, sodium hydroxide, or lithium hydroxide. As pointed out at line 53 in said column 4, one to three moles of base per mole of hydroxylamine is utilized in order to achieve acceptable reaction rates and yields. Since hydroxylamine is sensitive and decomposes in its free form, it is shipped as a salt, e.g., hydroxylammonium sulfate. The free hydroxylamine is liberated upon treatment of the salt with a base, such as ammonium hydroxide or sodium hydroxide.

The oximation reaction shows that the rate is interrelated to pH. The rate of reaction decreases as the pH is either raised or lowered. The addition of the base to aqueous hydroxylammonium sulfate produces, via a buffering effect, a suitable pH. As previously indicated, this reaction is known in the art.

In a commercial operation for the manufacture of APAP, according to the Beckmann rearrangement of the corresponding ketoxime, there is provided a single pass operation regarding the production of 4-HAP oxime from 4-HAP by treating the same with HAS and caustic. However, substantial quantities of an unwanted by-product, e.g., $Na_2SO_4$, are produced. Unexpectedly, we have found that the conversion of 4-HAP to 4-HAP oxime can be accomplished by subjecting the 4-HAP to suitable ammoximation conditions to form the 4-HAP oxime without any substantially unwanted by-products.

In general, the present invention covers a catalytic process for preparing 4-HAP oxime by reacting 4-HAP with $NH_3$ and an oxidizing agent, such as $H_2O_2$, in the liquid phase, or under other suitable ammoximation conditions, characterized in that the catalyst consists substantially of a molecular sieve, preferably titanium-containing molecular sieve such as a highly crystalline, $SiO_2$-containing substance having a zeolite structure, and, in particular, of a titanium-silicalite, optionally in admixture with an inert binder. The reaction temperature is generally greater than 0° C., and preferably from 25° C. to 150° C., and more preferably from 40° C. to 120° C. Titanium-silicalites are known compounds described, for example, in British Patent Nos. 2,024,790 and 2,071,071 and in U.S. Pat. No. 4,410,501. A pressure higher than the atmospheric pressure promotes the development of the reaction.

Other substances of zeolitic nature which can catalyze this highly useful reaction are, first of all, the various types of silicalite among which, e.g., silicalite I (see, for example, U.S. Pat. No. 4,061,724), silicalite II, zirconium-silicalites and hafnium-silicalites. Another class of analogous catalysts are the metal-silicates, for example, borosilicates (boralites), beryllo-silicates, chromosilicates, vanadium-silicates, zirconium-silicates, gallium-silicates and ferro-silicates which are described in part in British Patent No. 2,024,790. A third class of catalysts, always of analogous type, consists of the known aluminum-silicates, universally known as "zeolites"; first of all the zeolites of type Y, the zeolites ZSM5, the zeolites of type ZSM 11 and the other zeolites ZSM described in European Patent Nos. 129,239; 141,514; and 143,642; as well as the zeolites MB 28 described in European Patent No. 21,445. Examples of suitable catalysts that are quite effective in the present invention process include TS-1, Ti-Al-Beta, and Ti-ZSM-48.

The synthesis can be carried out as either a batch or continuous process. When the synthesis is carried out in batch, it is advisable to use from 0.1 to 50 parts by weight (preferably from one to 20 parts by weight) of pure catalyst (binder excluded) for 100 parts by weight 4-HAP; if it is performed continuously, it is suggested to employ a space velocity from 0.1 to 100 kg/h of 4-HAP per kg of catalyst.

The mole ratio of 4-HAP to the oxidizing agent (e.g. $H_2O_2$) is generally at least 1:1, preferably from about 1:1 to about 4:1. $H_2O_2$ designates substantially 100% pure hydrogen peroxide (i.e. without dilution water). The mole ratio of ammonia to the oxidizing agent (e.g. $H_2O_2$) is generally greater than 1:1, preferably from about 4:1 to about 20:1.

Various types of solvents are suitable for this reaction and assist the facilitation thereof. Such solvents include water and organic water-soluble solvents such as those which are capable of dissolving both pure ammonia and its water solutions. Examples of such organic water-soluble solvents include methanol, ethanol, propanol, isopropanol, n-butanol, i-butanol, t-butanol, and mixtures thereof. Other suitable solvents include, without limitation, acetonitrile, THF (tetrohydrofuran) and TFE (2,2,2-trifluoroethanol).

It is preferred to add ammonia before hydrogen peroxide, otherwise undesired side reactions occur. The mole ratio of ammonia to 4-HAP is generally greater than 1:1 and preferably from about 1:1 to about 20:1. At the end of the reaction, the 4-HAP oxime can be separated by different methods, for example, through extraction with suitable solvents (such as methylene dichloride and toluene), whereby a hydrophobic organic phase and an aqueous phase are formed. 4-HAP oxime and unreacted 4-HAP form the organic layer; the aqueous layer which contains the excess of $NH_3$ as well as traces of 4-HAP and of oxime, can be usefully recycled to the reaction section (ammoximation section).

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLES 1–4

An autoclave, equipped with a stirrer and a heating jacket, was first blanketed with an inert gas (nitrogen). Subsequently, there was charged (a) 0.3 grams of a catalyst consisting of a finely ground powder of titanium-silicalite containing 3.85% by weight of titanium dioxide (highly crystalline and having an average diameter of the particles $\geq 5$ um) commercially designated as TS-1 and sold by Enichem SpA (Italy); (b) 1.36 grams (10 mmol) 4-HAP; (c) 1.1 grams (10 mmol hydrogen peroxide) 30 weight percent hydrogen peroxide in water; (d) 2.9 grams (42 mmol ammonia) 25 weight percent ammonia in water; and (e) 3.2 grams t-butanol. The reaction mass was stirred and heating was started by conveying a liquid at 80° C. into the heating jacket. The stirring and heating were maintained for five hours, and then the heating was terminated and the entire reaction was cooled. The resulting suspension was filtered and the liquid portion was analyzed by HPLC (Nucleosil C18, THF/$H_2O$/TFA eluent [4/96/0.1]) and by iodometry for hydrogen peroxide. The results are disclosed in Table I below.

The procedure of Example 1 was repeated three times except other titanium molecular sieves (catalysts) are used: Example 2—Ti-Al-Beta; Example 3—Ti-ZSM-48; Example 4—no catalyst (blank). The results are set forth in Table I below.

Hydroquinone (HQ) is produced as a side-product due to the competitive Dakin oxidation of 4-HAP in the liquid phase under alkaline conditions.

TABLE 1

| Example No. | Catalyst | 4-HAP Conversion % | $H_2O_2$ Conversion % | 4-HAP Oxime Selectivity %[a] | Hydroquinone Selectivity %[a] | 4-HAP Oxime Yield %[a] |
|---|---|---|---|---|---|---|
| 1 | TS-1 | 55 | 100 | 41 | 52 | 23 |
| 2 | Ti-Al-Beta | 43 | 100 | 5 | 45 | 2 |
| 3 | Ti-ZSM-48 | 38 | 100 | 0 | 100 | 0 |
| 4 | Blank | 51 | n.d | 2 | 100 | <1 |

Note: [a]based on 4-HAP conversion

EXAMPLES 5–10

The procedure set forth in Example 1 was repeated except that the mole ratio of 4-HAP to $H_2O_2$ was varied and also the reaction time was varied. These results are disclosed in Table 2 wherein it can be seen that the hydroquinone formation was substantially decreased by use of a higher 4-HAP to $H_2O_2$ mole ratio than the 1:1 used in Example 1.

TABLE 2

| Example No. | 4-HAP/$H_2O_2$ Molar Ratio (Time/hr) | 4-HAP Conversion % | $H_2O_2$ Conversion % | 4-HAP Oxime Selectivity %[a] | Hydroquinone Selectivity %[a] | 4-HAP Oxime Yield %[a] |
|---|---|---|---|---|---|---|
| 5 | 4/1 (1) | 29 | 95 | 51 (64) | 2 | 15 (64) |
| 6 | 4/1 (2.5) | 25 | 100 | 73 (73) | 3 | 18 (73) |
| 7 | 4/1 (5) | 27 | 100 | 70 (76) | 0 | 19 (72) |
| 8 | 2/1 (2.5) | 36 | 88 | 68 (56) | 14 (12) | 24 (49) |
| 9 | 2/1 (5) | 44 | 100 | 54 (46) | 16 (14) | 24 (46) |
| 10 | 1/1 (5) | 55 | 100 | 41 (23) | 52 (29) | 23 (23) |

Note: [a]selectivity based on 4-HAP (hydrogen peroxide) conversion.

EXAMPLES 11–15

The procedure of Example 1 was repeated except that the mole ratio of ammonia to $H_2O_2$ was varied as well as the amount of catalyst concentration, all as indicated in Table 3. The results of these examples are set forth in Table 3. The results show that the yield in 4-HAP oxime is dependent on the ammonia:hydrogen peroxide molar ratio.

TABLE 3

| Example Number | Catalyst | Ammonia: $H_2O_2$ Molar Ratio | Catalyst Conc. wt % | 4-HAP Conversion % | Hydroquinone Selectivity %[a] | 4-HAP Oxime Selectivity %[a] | Color |
|---|---|---|---|---|---|---|---|
| 11 | Blank[b] | 4:1 | 0 | 51 | 100 (51) | 0 | Brown |
| 12 | TS-1[b] | 4:1 | 3.4 | 55 | 52 (29) | 41 (23) | Brown |
| 13 | Blank[b] | 20:1 | 0 | 21 | 53 (14) | 0 | Brown |
| 14 | TS-1[c] | 20:1 | 1.4 | 50 | 0 | 100 (50) | Orange |
| 15 | TS-1[c] | 20:1 | 2.5 | 50 | 0 | 100 (50) | Orange |

Note: [a]selectivity based on 4-HAP (hydrogen peroxide) conversion. 100% hydrogen peroxide conversion in every reaction - [b]1.36 g (10 mmol) 4-HAP - 1.1 g (10 mmol hydrogen peroxide) 30 wt % hydrogen peroxide in water - 2.7 g (40 mmol ammonia) 25 wt. % ammonia in water - 3.2 g t-butanol - [c]0.67 g (5 mmol) 4-HAP - 0.58 g (5 mmol hydrogen peroxide) 30 wt % hydrogen peroxide in water - 6.8 g, (100 mmol ammonia) 25 wt % ammonia in water - 1.6 g t-butanol.

EXAMPLES 16–23

The procedure set forth in Example 1 was repeated with the exception that various organic solvents were used. The influence of the organic solvent in the ammoximation of 4-HAP over TS-1 is presented in Table 4. The organic solvent can be added to the reaction mixture to enhance the solubility of 4-HAP. The ammonia: hydrogen peroxide molar ratio was 4:1. The ammoximation can be performed over TS-1 in many water/organic solvent mixtures. 25% yield in 4-HAP oxime was obtained whether t-butanol, methanol, or trifluoroethanol was used. The 4-HAP oxime yield was somewhat increased if tetrahydrofuran was applied, but less relevant with acetonitrile/water or water as solvent.

TABLE 4

| Example No. | Solvent | 4-HAP Conversion % | Oxime Selectivity %* | Hydroquinone Selectivity %* | $H_2O_2$ Conversion %* | Oxime Yield %* |
|---|---|---|---|---|---|---|
| 16 | t-butanol | 55 | 41 | 52 | 100 | 23 |
| 17 | acetonitrile | 30 | 48 | 40 | 100 | 14 |
| 18 | water | 64 | 22 | 78 | 100 | 14 |
| 19 | THF | 52 | 68 | 32 | 97 | 35 |
| 20 | methanol | 66 | 33 | 62 | 100 | 22 |
| 21 | TFE | 59 | 39 | 61 | 98 | 23 |
| 22 | n-butanol | 48 | 40 | 60 | 98 | 19 |
| 23 | blank | 56 | <1 | 100 | 98 | <1 |

Note: 0.3 g catalyst - 1.36 g (10 mmol) 4-HAP - 1.1 g (10 mmol hydrogen peroxide) 30 wt % hydrogen peroxide in water - 2.7 g (40 mmol ammonia) 25 wt % ammonia in water - 4 ml solvent - T = 80° C. - t = 5 h.
[a]based on 4-HAP conversion - TFE: 2,2,2-trifluoroethanol.

TABLE 5

| Example Number | Ammonia Source (wt % $NH_3$) | 4-HAP Conversion % | $H_2O_2$ Conversion % | Oxime Selectivity %* | Oxime Yield %* |
|---|---|---|---|---|---|
| 24 | water (25) | 50 | 100 | 100 | 50 |
| 25 | methanol (15) | 33 | 100 | 100 | 33 |
| 26 | t-butanol (4.9) | 20 | 93 | 100 | 20 |

*Note: Based on 4-HAP conversion - 4-HAP:hydrogen peroxide molar ratio = 1:1 - 1.7 wt % catalyst - ammonia:hydrogen peroxide molar ratio = 20:1 - 30 wt % hydrogen peroxide in water.

EXAMPLES 24–26

The procedure disclosed in Example 1 was repeated with the exception that ammonia was dissolved in methanol or t-butanol. 4-HAP conversion was less compared to the ammoximation in aqueous ammonia solution. The results are disclosed in Table 5.

EXAMPLES 27–33

The procedure set forth in Example 2 was repeated in order to demonstrate the influence of the solvent, catalyst concentration, and ammonia:hydrogen peroxide molar ratio. The titanoaluminosilicate called titanium-aluminum-beta (Ti-Al-Beta) contains titanium atoms inserted in the silica-alumina framework [note JCS Chem. Commun. (1992) 589]. These results are set forth in Table 6. Table 6 depicts the performances of this catalyst in the ammoximation of 4-HAP under various hydrophobic conditions, ammonia:hydrogen peroxide molar ratio or catalyst concentration. The conversion of 4-HAP was improved when methanol instead of water was used as solvent for ammonia. Again, high ammonia:hydrogen peroxide ratio favored the selectivity in 4-HAP oxime. The catalyst concentration of 30 g.l$^{-1}$ was sufficient to perform the ammoximation reaction. Under high ammonia:hydrogen peroxide molar ratio and in the presence of ammonia dissolved in methanol, the catalytic performances of Ti-Al-Beta became close to those of TS-1 (note Table 5). When the ammoximation of 4-HAP was carded out in the presence of ammonia dissolved in t-butanol, Ti-Al-Beta still showed selectivity in 4-HAP oxime.

TABLE 6

| Example Number | Solvent | Ammonia/ H$_2$O$_2$ mol. ratio | Catalyst Conc. g.l$^{-1}$ | 4-HAP Conversion % | H$_2$O$_2$ Conversion % | Oxime Selectivity %* | HQ Selectivity %* |
|---|---|---|---|---|---|---|---|
| 27 | water | 20 | Blank | 21 | 100 | 0 | 50 (11) |
| 28 | water | 20 | 13 | 20 | 100 | 22 (4) | 45 (9) |
| 29 | water | 20 | 30 | 19 | 100 | 47 (9) | 53 (10) |
| 30 | methanol | 20 | 30 | 32 | 100 | 82 (29) | 9 (3) |
| 31 | methanol | 20 | 60 | 27 | 100 | 89 (26) | 0 |
| 32 | methanol | 4 | 30 | 37 | 100 | 45 (16) | 40 (14) |
| 33 | t-butanol | 4 | 30 | 10 | 94 | 100 (10) | 0 |

Note: 4-HAP:hydrogen peroxide molar ratio = 1:1 - 30 wt % hydrogen peroxide in water - T = 80° C. - t = 5 h - *:selectivity based on the substrate, (hydrogen peroxide) conversion.

EXAMPLES 34–36

The procedure set forth in Example 1 was repeated, with the exceptions that the catalyst was titanium-zeolite-socony-Mobil-n° 48 (Ti-ZSM-48) instead of TS-1, and the solvents were varied. The insertion of titanium in the aluminum-free ZSM-48 silica framework was first reported in 1992 (JCS Chem. Commun. 745). The framework of Ti-ZSM-48 is unidimensional. The dimensions of the channel openings of Ti-ZSM-48 are close to those of TS-1 (5.3×5.6, 5.1×5.5Å). Ti-ZSM-48 was prepared with 1,4-diaminobutane as structural agent. Crystallization of Ti-ZSM-48 was demonstrated by X-ray diffraction measurements. Calcination of the catalyst was first carded out at 530° C., then three times at 550° C. overnight. White catalyst powders were finally obtained, indicating the removal of diaminoalkane from the silica framework. Minor loss of crystallinity occured due to the heating treatment as observed by XRD analyses of the calcined catalysts. The activity of the Ti-ZSM-48 catalyst in the ammoximation of 4-HAP are disclosed in Table 7.

TABLE 7

| Example No. | Substrate | Ammonia Dissolved in: | Substrate Conversion % | HQ Selectivity % | Oxime Selectivity % | Color |
|---|---|---|---|---|---|---|
| 34 | 4-HAP | methanol | 17 | 31 | 67 | Brown |
| 35 | 4-HAP | t-butanol | 16 | Trace | 50 | Orange |
| 36 | 4-HAP | water | 8 | 77 | 0 | Brown |

Note: Selectivities based on the substrate conversion - 100% hydrogen peroxide conversion. Ammonia:hydrogen peroxide molar ratio = 20:1 - 4-HAP:hydrogen peroxide molar ratio = 1:1 - 30 g catalyst.l$^{-1}$ - T = 80° C. - t = 5 h.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing 4-hydroxyacetophenone oxime which comprises reacting 4-hydroxyacetophenone with ammonia and hydrogen peroxide at a temperature from about 25° C. to about 150° C. in the presence of a catalyst comprising a titanium-containing molecular sieve.

2. The process according to claim 1 wherein the catalyst is a titanium-silicalite catalyst.

3. The process according to claim 1 wherein the molar ratio of ammonia to 4-hydroxyacetophenone is greater than about one and the temperature of reaction is from 40° C. to 120° C.

4. The process according to claim 1 wherein the molar ratio of ammonia to hydrogen peroxide is greater than 1.0.

5. The process according to claim 2 wherein a portion of the titanium-silicalite is replaced by zirconium-silicalite.

6. The process according to claim 1 wherein there is also included an organic solvent.

7. The process according to claim 1 wherein the catalyst is selected from the group consisting of TS-1, Ti-Al-Beta, and Ti-ZSM-48.

8. A process for the preparation of 4-hydroxyacetophenone oxime which comprises reacting 4-hydroxyacetophenone with ammonia and hydrogen peroxide under the following conditions:

a. the reaction temperature is from about 40° C. to about 120° C.;
   b. the mole ratio of 4-hydroxyacetophenone to hydrogen peroxide is from about 1:1 to about 4:1;
   c. the mole ratio of ammonia to hydrogen peroxide is from about 4:1 to about 20:1;
   d. the mole ratio of ammonia to 4-hydroxyacetophenone is from about 1:1 to about 20:1;
   e. there is also included a titanium-containing molecular sieve catalyst having a highly crystalline, silicon dioxide-containing substance having a zeolite structure.

9. The process according to claim 8 wherein there is also included an organic water-soluble solvent.

10. The process according to claim 9 wherein said catalyst is selected from the group consisting of TS-1, Ti-Al-Beta, and Ti-ZSM-48.

\* \* \* \* \*